United States Patent [19]

Kondo

[11] Patent Number: 5,025,804
[45] Date of Patent: Jun. 25, 1991

[54] ENDOSCOPE ANGLING MECHANISM

[75] Inventor: Mituo Kondo, Omiya, Japan

[73] Assignee: Fuji Photo Optical Co., Ltd., Omiya, Japan

[21] Appl. No.: 550,640

[22] Filed: Jul. 10, 1990

[30] Foreign Application Priority Data

Jul. 12, 1989 [JP] Japan ................................... 1-177945

[51] Int. Cl.$^5$ ............................................... A61B 1/00
[52] U.S. Cl. .......................................................... 128/4
[58] Field of Search ........................................... 128/4

[56] References Cited

U.S. PATENT DOCUMENTS

| | | | |
|---|---|---|---|
| 4,483,326 | 11/1984 | Yamaka et al. | 128/4 |
| 4,718,407 | 1/1988 | Chikama | 128/4 |
| 4,841,951 | 6/1989 | Umeda | 128/4 |

Primary Examiner—William H. Grieb
Attorney, Agent, or Firm—Oblon, Spivak, McClelland, Maier & Neustadt

[57] ABSTRACT

An endoscope angling mechanism which is provided with: an angle operating means including a pair of first and second operating wires to be pulled to and fro for arcuately bending an angle portion of joint ring structure at the distal end of an insert section extending contiguously from an operating section of an endsoscope, the first operating wire having the fore end thereof securely stopped on an angle ring in the foremost position in the angle portion or to a rigid portion at the distal end of the angle portion and the second operating wire having the fore end thereof securely stopped on an angle ring in a position posterior to and spaced from the foremost angle ring by a predetermined number of angle rings; and a restraining means for restraining forward movement of the second operating wire in angling operation until operated with a predetermined increased force.

8 Claims, 3 Drawing Sheets

ENDOSCOPE ANGLING MECHANISM

BACKGROUND OF THE INVENTION

1. Field of the Invention

This invention relates to an endoscope angling mechanism for bending a rigid portion at the tip end of an insert section of an endoscope arcuately into desired directions.

2. Description of the Prior Art

Endoscopes are in wide use for medical and industrial purposes, for example, for internal examination or diagnosis of patients' bodies, engines, nuclear reactors or other equipments, or for therapeutic or repairing treatments with use of concurrently inserted forceps or other instruments.

For understanding the status of the prior art, FIGS. 7 and 8 schematically illustrate the general construction of an endoscope of this sort and the construction of a prior art angling mechanism, respectively. In these figures, indicated at 1 is an insert section and at 2 is an operating section of the endoscope. The insert section 1 is successively composed of: a flexible portion 1a which forms a major part of the insert section 1 in proportion, extending contiguously from the operating section 2 of the endoscope and being smoothly flexible in conformity with the shape of the path of insertion of the endoscope; an angle portion 1b connected to the fore end of the flexible portion 1a; and a rigid tip end portion 1c connected to the fore end of the angle portion 1b.

In this instance, the angle portion 1b has a joint ring structure which is composed of a plural number of pivotally connected angle rings 3 and which can be bent in a desired direction. Namely, the rigid portion 1c at the distal end can be turned into a desired direction when introducing the insert section 1 into a body along a path of insertion or when changing the field of view of observation. For bending the angle portion 1b in this manner, an angling mechanism is provided in association with a knob section to be manipulated by the operator.

As shown in FIG. 8, the angling mechanism of this sort usually employs a pair of upper and lower operating wires 4a and 4b (or a pair of upper and lower wires plus a pair of left and right wires) within the angle rings 3 in the angle portion 1b. Each of these operating wires 4a and 4b has the fore end thereof securely stopped on an angle ring 3a in the foremost position (or to the distal end of the rigid portion 1c), and the other end extended into the operating section 2 and wound on an angle drum 5. The angle drum 5 is mounted on a rotational shaft 6 which is led out of the housing of the operating section 2 and coupled with an angle knob 7. Accordingly, as the angle knob 7 is turned by an operator, the operating wires 4a and 4b are pulled to and fro to bend the angle portion 1b as indicated by imaginary line in FIG. 7.

However, in a case where the angle portion 1b is arranged to be bent in its entirety by the angling operation as described above, difficulties are encountered, for example, in changing the field of view of observation in a narrow intracorporeal cavity or the like. For the purpose of overcoming such a problem, there has been developed an endoscope with an angle portion 1b which has a higher rigidity toward its base end in such a way that it is bendable only in its fore end portion in an initial stage of the angling operation and becomes bendable toward the rigid base end portion and finally in its entire body in proportion to the magnitude of the applied angling efforts. This angle construction has a problem that the load of the angling operation is increased to such an extent as to impair smooth operation of the angle knob.

SUMMARY OF THE INVENTION

The present invention contemplates to overcome the above-mentioned problems or drawbacks, and has as its object the provision of an endoscope angling mechanism which can improve the operationability of the angle portion of an endoscope.

It is another object of the present invention to provide an endoscope angling mechanism which can bend only the fore end portion of the angle portion, if necessary, smoothly in a facilitated manner.

It is still another object of the invention to provide an endoscope angling mechanism which can change the field of view of observation easily even in a narrow space like an intracorporeal cavity.

In accordance with the present invention, the above-stated objectives are achieved by an endoscope angling mechanism which is provided with: an angle operating means including a pair of first and second operating wires to be pulled to and fro for arcuately bending an angle portion of joint ring structure at the distal end of an insert section extending contiguously from an operating section of an endoscope, the first operating wire having the fore end thereof securely stopped on an angle ring in the foremost position in the angle portion or to a rigid portion at the distal end of the angle portion and the second operating wire having the fore end thereof securely stopped on an angle ring in a position posterior to and spaced from the foremost angle ring by a predetermined number of angle rings; and a restraining means for restraining forward movement of the second operating wire in angling operation until operated with a predetermined increased force.

The above and other objects, features and advantages of the invention will become apparent from the following description and the appended claims, taken in conjunction with the accompanying drawings showing by way of example preferred embodiments of the invention.

BRIEF DESCRIPTION OF THE DRAWINGS

In the accompanying drawings:

FIGS. 1 through 4 illustrate a first embodiment of the invention, of which FIG. 1 is a schematic view of an angling mechanism as a whole, FIG. 2 is a partly sectioned schematic view of a restraint mechanism, and FIGS. 3 and 4 are schematic fragmentary views adopted for explanation of the angling operation;

FIGS. 5 and 6 illustrate a second embodiment of the invention, of which FIG. 5 is a schematic fragmentary view of major components of an angle operating mechanism, and FIG. 6 is a schematic front view of a lever member; and FIGS. 7 and 8 illustrate a conventional counterpart, of which FIG. 7 is a schematic view showing the general construction of an endoscope, and FIG. 8 is a schematic view of the conventional angle operating mechanism.

DESCRIPTION OF PREFERRED EMBODIMENTS

Figure 1:
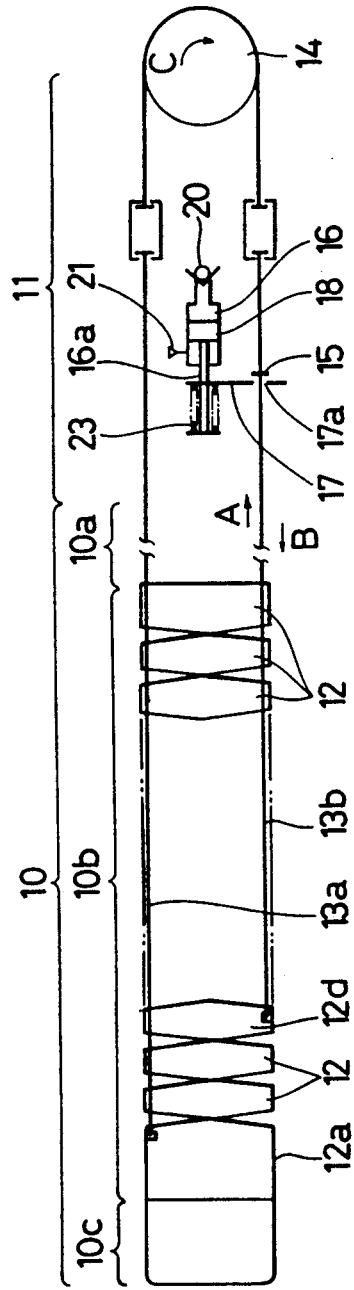

Hereafter, the invention is described more particularly by way of the preferred embodiments shown in the drawings.

Referring first to FIGS. 1 through 4, there is shown a first embodiment of the invention, in which indicated at 10 is an insert section and at 11 is an operating section of an endoscope. The references 10a, 10b and 10c denote a flexible portion, an angle portion and a rigid tip end portion of the insert section 10, respectively.

The angle portion 10b has a joint ring structure which is composed of a plural number of flexibly connected angle rings 12. A pair of operating wires 13a and 13b are inserted in the angle portion along the inner surface thereof, such that the angle portion 10b is bent upward or downward in FIG. 1 by pulling one of the operating wires in the rearward direction and the other wire in the forward direction. The rear ends of these operating wires 13a and 13b are stopped on an angle drum in the same manner as in the prior art angling mechanism mentioned hereinbefore.

The fore end of one of these operating wires 13a and 13b, for example, of the first operating wire 13a is securely stopped on an angle ring 12a in the foremost position in the angle portion 10b, while the fore end of the other or the second operating wire 13b is securely stopped on an angle ring 12d which is located in a position posterior to and spaced from the foremost ring 12a by a predetermined number of angle rings, more specifically, to an angle ring 12d in the fourth position in this particular embodiment.

Further, the second operating wire 13b is provided with a bulged portion 15 within the housing of the operating section 11 for cooperating with a restraint means which is provided also in the housing of the operating section 11, including a piston cylinder 16 for restraining forward movement of the second operating wire 13b. Piston rod member 16a of the cylinder 16 is connected to a blocking plate 17 with an aperture 17a through which the second operating wire 13b is passed and freely movable except the bulged portion 15. Accordingly, the second operating wire 13b is freely passable through the aperture 17a when it is pulled for movement in the direction of arrow A in FIG. 1, but its displacement is restrained by abutting engagement of the bulged portion 15 against the blocking plate 17 when it is pushed forward as indicated by arrow B in the same figure.

In this instance, a vacuum chamber 19 is defined in the cylinder 16 by a piston 18 which is connected to the rod 18a. This vacuum chamber 19 is provided with a check valve 20 which permits outflow of air to the atmosphere but blocks inflow of air into the vacuum chamber 19. The cylinder 16 is provided with an aperture 21 in its peripheral wall, so that the pressure in the vacuum chamber 19 is lowered by expansion when the piston 18 is moved forward from a rear end end position in the cylinder 16, until the piston 18 clears the aperture 21. Therefore, the forward movement of the piston 18 is firstly met by a large resistance, which however drops markedly as soon as the piston 18 is moved forward beyond the position of the aperture 21. In order to prevent an abrupt drop of the resistance, the piston 18 is provided with a V-groove 22 which constitutes a variable orifice. Further, the blocking plate 17 is biased toward the rear end wall of the cylinder 16 by a return spring 23 which pushes back the piston 18 toward the rear end wall of the cylinder upon removing the pushing efforts on the second operating wire 13b.

In this embodiment, by turning the angle drum 14 in the direction of arrow C in FIG. 1, the first operating wire 13a is pulled toward the angle drum 14 while the second operating wire 13b is pushed away from the drum. At this time, the bulged portion 15 of the pushed second operating wire 13b is abutted against the marginal edges of the aperture 17a in the blocking plate 17 to push the latter in the direction of arrow B. As a result, the rod 16a is moved in the same direction together with the blocking plate 17, accompanied by a forward movement of the piston 18 which is connected to the rod 16a, lowering the pressure in the vacuum chamber 19 through expansion and increasing the resistance to the pushing efforts on the second operating wire 13b to restrain its forward movement. Therefore, of the angle rings 12 in the angle portion 10b, the angle rings which are in positions rearward of the angle ring 12d, to which the fore end of the second operating wire 13b is connected, are retained in a rectilinear form while the angle rings 12 forward of the angle ring 12d are bent arcuately by the tension of the first operating wire 13a. Consequently, as shown particularly in FIG. 3, the the angle portion 10b is bent to one side in its fore end portion alone. This permits the operator to change the field of observation extremely easily and smoothly even in a narrow intracorporeal cavity or the like.

Now, upon rotating the angle drum 14 further from that position, the piston 18 is displaced further in the forward direction by the increased pushing efforts on the second operating wire 13b, clearing the aperture 21 in the peripheral wall of the cylinder 16. Whereupon, the vacuum chamber 19 is opened to the atmosphere and put in no-load condition, permitting the operator to push forward the second operating wire 13b with ease. As a result, as shown in FIG. 4, the entire angle portion 10b is bent arcuately as in an ordinary angling operation.

Although an extra operating force is required to compress the return spring 23 for bending the whole angle portion 10b, the angle drum 14 can be operated easily under a relatively light load by employing a return spring 23 with a minimum necessary spring force for returning the piston 18 to the rear position when the bulged portion 15 is disengaged from the blocking plate 17.

Figure 3:
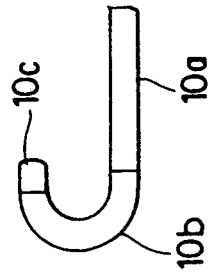
Figure 4:
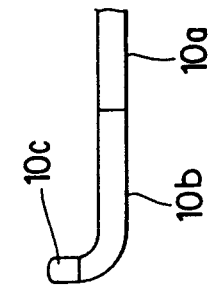
Figure 2:
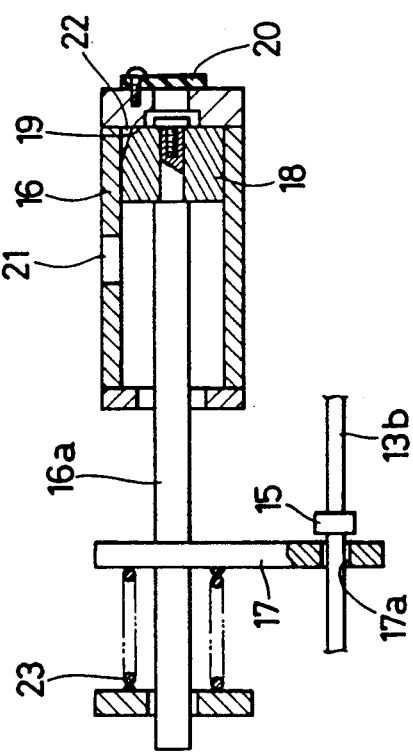

Upon communication with the atmosphere of the vacuum chamber 19 of the cylinder 16, the second operating wire 13b is relieved of the restraining action of the cylinder 16 of the restraining means, and the angle portion 10b as a whole becomes bendable as shown in FIG. 4 in contrast to the restrained state where only its fore end portion is bendable as shown in FIG. 3. At this time, for the purpose of precluding dangerous abrupt bending of the angle portion 10b, the V-groove 22 which is provided on the piston 18 as a variable orifice prevents a sudden pressure change in the vacuum chamber 19 and thus ensures smooth cancellation of the restraining action.

If the angle drum 14 is returned to its initial position, the blocking plate 17 is moved in the direction of arrow A by the action of the return spring 23, pushing the piston 18 back to a position in the proximity of the rear end of the cylinder 16. At this time, the volume of the vacuum chamber 19 is reduced smoothly as air in the vacuum chamber 19 is discharged to the atmosphere through the check valve 20.

On the other hand, when the angle portion 10b is to be bent in the opposite direction, namely, when the second operating wire 13b is pulled toward the drum 14 while pushing forward the first operating wire 13a, the bulged portion 15 is moved away from the blocking plate 17 so that the whole angle portion 10b is bent arcuately free of any restraint force.

Figure 5:
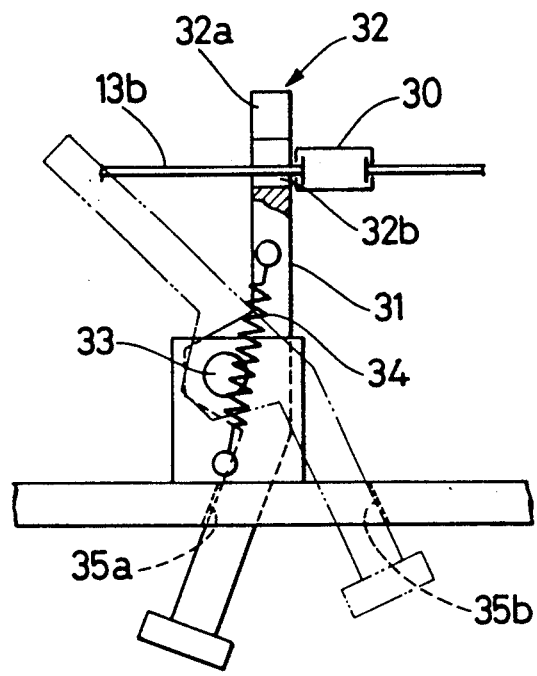
Figure 6:
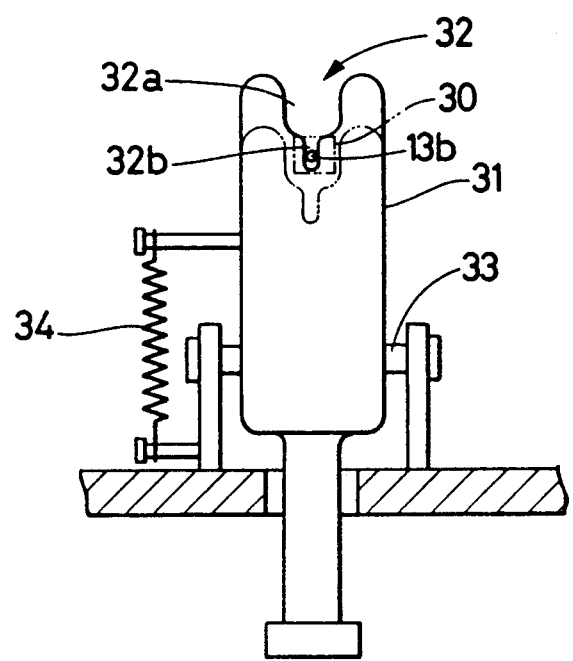
Figure 7:
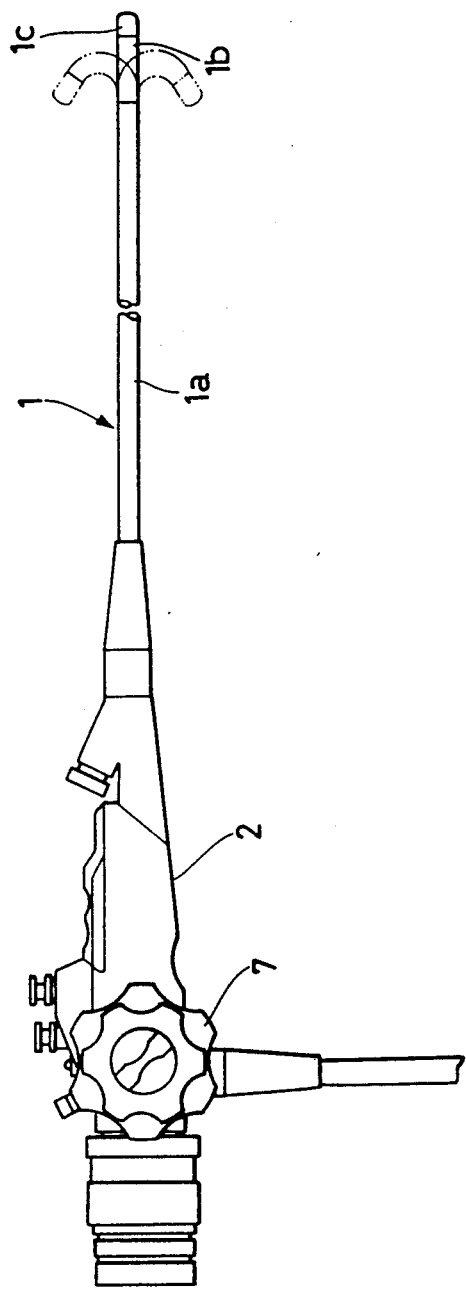
Figure 8:
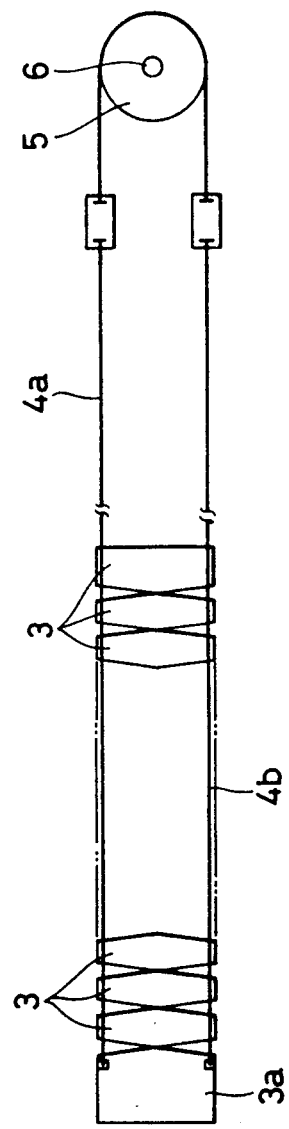

Referring now to FIGS. 5 and 6, there is shown a second embodiment of the invention, in which the component parts identical or equivalent to the corresponding parts in the first embodiment are designated by similar reference numerals. Explanation of the identical or equivalent parts is omitted in the following description to avoid repetitions.

In this embodiment, the restraining means is constituted by a lever 31 which is engageable with one of anti-slackening sleeves 30 of the first and second operating wires 13a and 13b. The lever 31 is formed with a slit 32 for passing the second operating wire 13b therethrough. More specifically, as shown in FIG. 6, the slit 32 is provided with a broad slit portion 32a for passing the sleeve 30 and a narrow slit portion 32b for blocking passage of the bulged portion 15. The lever 31 is rockable about a shaft 33 back and forth in the direction of movement of the wire 13b, and, under the influence of the action of a toggle spring 34, capable of assuming a restraining position where the operating wire 13b is located in the narrow slit portion 32b and a relieving position where the operating wire 13b is located in the broad slit portion 32a. Stoppers 35a and 35b are provided for holding the lever 31 in the restraining and relieving positions, respectively. The outer end of the lever 31 is projected to the outside through the housing of the operating section 11 to be gripped in the operator's hand, so that the operator can operate the lever 31 with a finger.

With this arrangement, if the lever 31 is held in the restraining position in an angling operation, the forward displacement of the second operating wire 13b is restrained by the engagement of the sleeve 30 with the narrow slit portion 32b of the lever 31, permitting to bend only a fore end portion of the angle portion 10b. When the lever 31 is tilted into the relieving position, the sleeve 30 is allowed to pass the broad slit portion 32a of the lever 31, so that the whole angle portion 10b can be bent arcuately.

In the foregoing embodiments, the fore end of one operating wire 13a is stopped on the angle ring 12a in the foremost position in the angle portion 10b while the fore end of the other operating wire 13b is stopped to the angle ring 12d in the fourth position. However, it is also possible to stop one operating wire on the rigid tip end portion 10c, while stopping the other or second operating wire 13b on an angle ring in a suitable posterior position depending upon the intended bending angle of the rigid tip end portion 10c. In this connection, the bending angle can be increased by stopping the fore end of the second operating wire 13b to an angle ring in a position closer to the base end of the angle portion 10b, although such arrangements often result in a difficulty of bending the entire body of the angle portion 10b smoothly into an arcuate form. In such a case, it is advisable to add another operating wire along the second operating wire 13b, stopping the fore end of the additional operating wire on the foremost angle ring 12a or on the rigid tip end portion 10c and the rear end on the angle drum. In addition to the particular examples shown and described herein, the restraint force may be applied by the use of a magnetic clamp means, frictional clamp means, resisting means employing a spring or the like.

What is claimed is:

1. An endoscope angling mechanism, comprising:
   an angle operating means having a pair of first and second operating wires adapted to be pulled to and fro for bending an angle portion of a joint ring structure at the distal end of an insert section extending contiguously from the fore end of an operating section of an endoscope, said first operating wire having the fore end thereof securely stopped on one of an angle ring in the foremost position in said angle portion, and a rigid tip end portion of said angle portion, said second operating wire having the fore end thereof securely stopped on an angle ring in a position posterior to and spaced from the foremost angle ring by a predetermined number of angle rings; and
   a restraining means for restraining forward movement of said second operating wire in angling operation until operated with a predetermined increased force.

2. An endoscope angling mechanism as defined in claim 1, wherein said first and second operating wires are extended along the upper and lower sides of said insert section, and said restraining means is provided in association with said second operating wire on the lower side.

3. An endoscope angling mechanism as defined in claim 1 or 2, further comprising another pair of similar operating wires in laterally opposite positions in addition to said first and second operating wires.

4. An endoscope angling mechanism as defined in claim 1, wherein said restraining means is provided with a piston cylinder defining a vacuum chamber and an atmospheric chamber on the opposite sides of a piston, and a blocking plate connected to the piston rod of said cylinder and adapted to engage a bulged portion of said second operating wire to restrain forward wire movement until said vacuum chamber is opened to the atmosphere.

5. An endoscope angling mechanism as defined in claim 4, wherein said piston is provided with a V-groove on the circumferential surface thereof to serve as a variable orifice for gradually opening said vacuum chamber with the atmosphere when said piston is displaced in said cylinder.

6. An endoscope angling mechanism as defined in claim 1, wherein said restraining means is provided with a switchable blocking member capable of assuming a restraining position to restrain forward movement of said second operating wire by engagement with a bulged portion on the latter.

7. An endoscope angling mechanism as defined in claim 6, wherein said blocking member is in the form of a lever, rockable between a restraining position in abutting engagement with said bulged portion on said second operating wire and a relieving position disengaged from said bulged portion.

8. An endoscope angling mechanism as defined in claim 7, wherein said restraining means further comprises a toggle spring for stably retaining said blocking member in said restraining and relieving positions.

* * * * *